US008639362B2

United States Patent
Zahler

(10) Patent No.: US 8,639,362 B2
(45) Date of Patent: Jan. 28, 2014

(54) POST-OPERATIVE PECTORAL-POCKET IMMOBILIZATION DEVICE

(76) Inventor: Byron Zahler, Portland, OR (US)

( * ) Notice: Subject to any disclaimer, the term of this patent is extended or adjusted under 35 U.S.C. 154(b) by 186 days.

(21) Appl. No.: 12/952,375

(22) Filed: Nov. 23, 2010

(65) Prior Publication Data

US 2011/0125242 A1 May 26, 2011

Related U.S. Application Data

(60) Provisional application No. 61/264,167, filed on Nov. 24, 2009.

(51) Int. Cl.
- *A61N 1/00* (2006.01)
- *A61N 1/39* (2006.01)
- *A61F 5/00* (2006.01)
- *A61F 5/28* (2006.01)

(52) U.S. Cl.
USPC ............... 607/149; 607/1; 607/2; 128/105.1; 602/4; 602/20; 602/21

(58) Field of Classification Search
USPC .................. 607/112, 149, 1, 2; 602/4, 20, 21; 128/105.1
See application file for complete search history.

(56) References Cited

U.S. PATENT DOCUMENTS

| 3,780,729 | A | * | 12/1973 | Garnett | 602/4 |
| 5,976,099 | A | * | 11/1999 | Kellogg | 602/23 |
| 6,095,936 | A | | 8/2000 | Kirkpatrick et al. | |
| 6,979,303 | B2 | | 12/2005 | Jestrabek-Hart | |
| 2008/0029104 | A1 | | 2/2008 | Vanderpool | |

* cited by examiner

*Primary Examiner* — Niketa Patel
*Assistant Examiner* — Lindsey G Hankins
(74) *Attorney, Agent, or Firm* — Peter A. Haas Esquire LLC

(57) ABSTRACT

The present invention comprises a chest band adapted to encircle the torso of a patient after having implant surgery. The chest band couples to an arm cuff by means of an adjustable strap. The arm cuff fits loosely over the patient's arm above the elbow and is adjustable, comprising a single strap material with mating hook and loop fastener devices to allow adjustability for different sized arms. The chest band had a tapered end that over folds a second end and the tapered end includes a hook and loop faster that releasably couples directly to the fabric of the chest band. An adjustable wrist cuff includes a direct means for fastening the cuff to the chest band, or optionally, a second adjustable strap to enable selective coupling of the wrist cuff to the chest band.

9 Claims, 5 Drawing Sheets

POST-OPERATIVE PECTORAL-POCKET IMMOBILIZATION DEVICE

PRIORITY CLAIM

The present application claims benefit under 35 USC Section 119(e) of U.S. Provisional Patent Application Ser. No. 61/264,167 filed on 24 Nov. 2009: The present application is based on and claims priority from this application, the disclosure of which is hereby expressly incorporated herein by reference.

BACKGROUND

The present invention relates to externally worn restraint devices for the upper torso including the arm, wrist and shoulder of a human patient, particularly as such devices are used to restrict or restrain arm and shoulder movement after pacemaker or ICD (implantable cardiac defibrillator) implant surgery.

Pacemakers and ICD's are small devices implanted usually below the left or right clavicle/collar bone. They are usually placed in a formed pocket subcutaneous (below the skin). Wire leads are connected to the implanted device and placed inside the heart through appropriate blood vessels. Multiple leads can be placed in the left ventricle, right ventricle, and right atrium. The collection of leads and the implanted device form a system, which is sutured to the skin in the pocket at an access point below the left or right clavicle. It is very important that the system remain stable during healing time, which typically lasts anywhere from up to 6 weeks.

It is crucial to patient recovery for the system to remain stable during this healing time to prevent lead dislodgment. Most lead dislodgements occur before 3 weeks, but can occur months later. If a lead is pulled out, this causes major complications whereas a revisit to the OR/Cath Lab is required and the lead is reset and repositioned. The patient then faces an increased chance of infection. It is noted that each time a patient undergoes surgery for a battery generator change or a lead reposition, there is a 3% increase in chance of infection. This is also very costly to the patient and the hospital, requiring another overnight stay and more medication for the additional procedure.

To reduce the potential of dislodgement, some physicians leave a little extra wire in the heart. However, this may lead to other complications including valve dysfunction and pro arrthymic conditions.

Some physicians prescribe external restraint devices. These devices are designed to restrict movement of the patient's arm and shoulder relative to the torso. Routinely used is an arm sling to immobilize the shoulder. Arm slings are extensively used to protect and/or support an arm following an injury or sickness and a variety of arm slings are well known. For example, U.S. Pat. No. 6,770,044 issued to Joslin on 3 Aug. 2004 is characteristic of such slings that form a pouch into which the forearm can be placed, allowing the hand to partially or fully extend from the front end of the pouch and provides a cradle or pocket to rest the elbow. A strap secures to the pouch and is slung over the wearer's neck and shoulder to support the sling in relative vertical position relative to the wearer's torso. However, horizontal (away from the torso) movement is not restricted except by the practical physical limitations of the strap. Thus, when such a typical sling is used post implant surgery, there is inadequate restriction of movement and the lead wires can become dislodged. With a traditional shoulder sling, there is also the very real chance of "muscular atrophy" and "frozen shoulder".

Another attempt to reduce arm movement includes the apparatus disclosed by Vanderpool in U.S. Pat. App. No. 2008/0029104A1 published on 7 Feb. 2008. The Vanderpool apparatus includes several stout rubber bands linked together. One end of the linked bands attaches to a belt worn about the waist of the patient, and the other end attaches to the wrist of the restrained arm of the patient. Thus, by varying the length of the rubber bands linked together, the range of motion of the restrained arm can be limited relative to the torso. However, the Vanderpool device does not contemplate restricting movement of the shoulder or upper arm.

Yet another known restraining device includes the arm sling apparatus allowing movement or total immobilization disclosed by Jestrabek-Hart in U.S. Pat. No. 6,979,303 issued on 27 Dec. 2005. The Jestrabek-Hart apparatus includes a cooperating suspension system and support frame to transfer the weight of the arm to the torso allowing the shoulder to rest. The suspension system includes one or more suspending devices engages and supports the arm with a rigid support frame consisting of a stiff waist belt and rigid upright support arm. Immobilization straps adjust to permit varying degrees of immobility. However, the Jestrabek-Hard apparatus does not contemplate restricting movement to maintain leads from an implanted device and is of such complexity that it precludes the patient from self-adjusting, and precludes the patient from putting this apparatus on without assistance from a care giver. Moreover, the Jestrabek-Hard apparatus is costly to own and operate.

Kirkpatrick et al. in U.S. Pat. No. 6,095,936 issued on 1 Aug. 2000, teach an arm restrain apparatus for aiding basketball players, the apparatus comprising a first engaging member being attached to a waist, a second engaging member being attached to a forearm, and a flexible or resilient band interposed there-between, the resilient band being of a length sufficient to reduce or prevent movement of the arm above shoulder height. However, Kirkpatrick et al. expressly teach away from a device suitable for use to restrict arm movement to prevent lead displacement post-operatively—for instance, in FIGS. 5, 6 and 7, Kirkpatrick et al. illustrates moving the arm above the head—this could result in lead displacement.

Another shortcoming not contemplated in the present art is a lack of a sensor to detect excess movement and no warning device to alert the patient and or medical staff that the arm is about to move beyond a safe range in the restricted range of movement of the wearer.

Thus, there remains a need for a device that can easily be worn by a patient after implant surgery. The device should enable the recovering implant patient to put on or take off the device without any assistance of a caregiver or other person. Further, such an improved device should overcome the disadvantages known in the prior- and current-art. The device should enable the patient some movement of the arm and shoulder but still prevent the lead wires from moving inside the body. Additionally, the improved device should prevent patients from raising their shoulder and pulling/tearing the lead tip from the endocardium. And, such an improved device should discourage movement of the upper arm and shoulder, and wrist relative to the torso.

SUMMARY OF THE INVENTION

The present invention, in one preferred embodiment, is presently under development under the trade name Pace-Brace™ (a trademark of BZ Medical, Inc. of Portland, Oreg., USA) and comprises a restraint device for the upper torso including the shoulder, wrist, and arm. As such, this particular preferred embodiment of the present invention is primarily designed for use following invasive surgery typical for implanting a pacemaker or implantable cardiac defibrillator (ICD).

Some features and benefits of this embodiment include:

Adjustable connections for chest, arm, and wrist based on the treating physician's preference as to how to treat individual patients—both arm and wrist cuffs are adjustable.

Fixed connection for chest, wrist, and arm to enable the physician to select location;

Added retraining strap to provide additional security, which is particularly important during early days post implant and/or to secure the arm during sleep or rest in such a way to immobilize or restrict the arm, shoulder and wrist;

A warning alarm for when arm is extended beyond designed elevation to remind patient; and Attractive—simple design/attractive and increases patient usage.

Additional features include a strap linking the arm cuff to the chest band by a strap that restricts motion to about 45 degrees vertically from the waist and prevents a 90-degree orientation of the arm. Although a stronger patient could force it to about 65 degrees and tear, the present invention prevents, resists, or otherwise discourages movement greater than that and especially prevents the disastrous 180 degrees (extending the arm straight upwards). Allows mobility to prevent muscular atrophy and frozen shoulder.

An added component of this preferred embodiment, an immobilizer strap extends over the arm and torso and fixes the arm in a downward position. This is particularly useful at night when the patient is asleep and prevents unwanted and unexpected movement of the arm.

The present invention is particularly suited to older people with heart problems. It is simple and easy to use. Other contemplated modifications include adding a sensor to audibly alert the wearer of motion that is beyond a preset limit.

Another feature is an adjustable arm cuff, which may intentionally be set "loose" to allow easy off/on.

The strap connecting the chest band to the arm cuff is adjustable and includes a hook and loop fastener to keep the loose end of the strap from dangling and for greater security.

A first preferred use or method of use of the preferred embodiment of the present invention includes restricting movement of the pectoral muscles after an implant surgery. The primary movement by pectoral muscles, contraction, occurs during horizontal adduction and internal rotation of the arm and shoulder (glenohumeral joint). Movements that stretch the pectoral muscles are external rotation and horizontal abduction. Contraction and stretching of the pectoral muscles can pull on the leads causing lead dislodgement. A leading cause for lead dislodgement is moving the shoulder backwards or upwards (stretching the pectoral muscles). Because of this action, an adjustable wrist cuff attaches by hook and loop fastener to the front of the chest band worn by the patient. This wrist cuff will restrict that backward and forward shoulder movement.

The big advantage of the PaceBrace™ post-operative pectoral pocket immobilization device is the adjustability for the arm and wrist. Patients can easily tighten it up early post op or at night, then release it outwards for secure safe and controlled passive movement of the shoulder joint. This movement will prevent contractures (adhesive capsulitis AKA frozen shoulder), a common complication with brace/sling usage for shoulder immobilization.

A preferred embodiment of the present invention contemplates an arm and shoulder restrictor well suited for use following device pocket implants to reduce the possibility of lead dislodgement, muscular atrophy, and frozen shoulder and is available from BZ Medical Inc., of Portland, Oreg., USA and their associated web-site, www.pacebrace.com, as a product sold under the trademark "PaceBrace" brand arm and shoulder restrictor or immobilizer. This preferred embodiment includes of a chest band with arm and wrist cuffs. The arm cuff is positioned slightly above the elbow and is connected to the chest band with an adjustable strap that controls (restricts or immobilizes) shoulder and elbow movement. The optional wrist cuff attaches to the chest band and is used to help immobilize the arm and shoulder early post op and during sleep: The wrist cuff may also include as second adjustable strap to allow a confined amount of wrist and shoulder movement. Preferred materials for this embodiment's bands, cuffs, and straps include nylon, which is easily hand-washable with mild detergent in warm water and can air dry. This embodiment is available in multiple sizes including Small, which fits up to 36" diameter torsos, Medium fits up to 48" diameter torsos, and Large fits up to 60" diameter torsos—of course other sizes for smaller or larger individuals are also contemplated. There are two primary modes of use: Limited and Fixed modes.

When placing on a patient, or when a patient self-uses the device of this preferred embodiment in the initial fitting the arm cuff is first slipped over the wrist or wrapped around the upper arm. The arm cuff self-adheres by means of hook and loop fastener-type closure device but is placed loosely allowing the cuff to slide freely up and down the upper arm above the elbow and below the shoulder. The torso-support (chest) band is placed with the shorter end on the front portion of the torso and the longer end is wrapped around the back returning to the front passing under the arm opposite the cuffed-arm. The long end of the torso-support chest band self-adheres to the short end.

In the Limited Mode, which is likely used under direction of a physician, an adjustable strap connected to the arm cuff and extending to the chest is first pulled away from the (torso-support) chest band to release the hook and loop fastener, the strap is selectively positioned to allow the arm cuff to have a limited range of motion relative to the chest band, then the strap free end is secured to the chest band by a cooperating hook and loop-type fastener arrangement between the free end and the chest band.

In the Fixed Mode, which is likely to be worn early post operative and/or during sleep as directed by physician, a wrist cuff is worn over the patient's wrist along with the arm cuff. The arm cuff is secured against the chest band to restrict movement. And, the wrist cuff is placed on the chest band in front of the patient and secured in place by coupling the hook and loop fastener closure.

DRAWING

DESCRIPTION OF THE INVENTION

Possible embodiments will now be described with reference to the drawings and those skilled in the art will understand that alternative configurations and combinations of components may be substituted without subtracting from the invention. Also, in some figures certain components are omitted to more clearly illustrate the invention.

Figure 1:
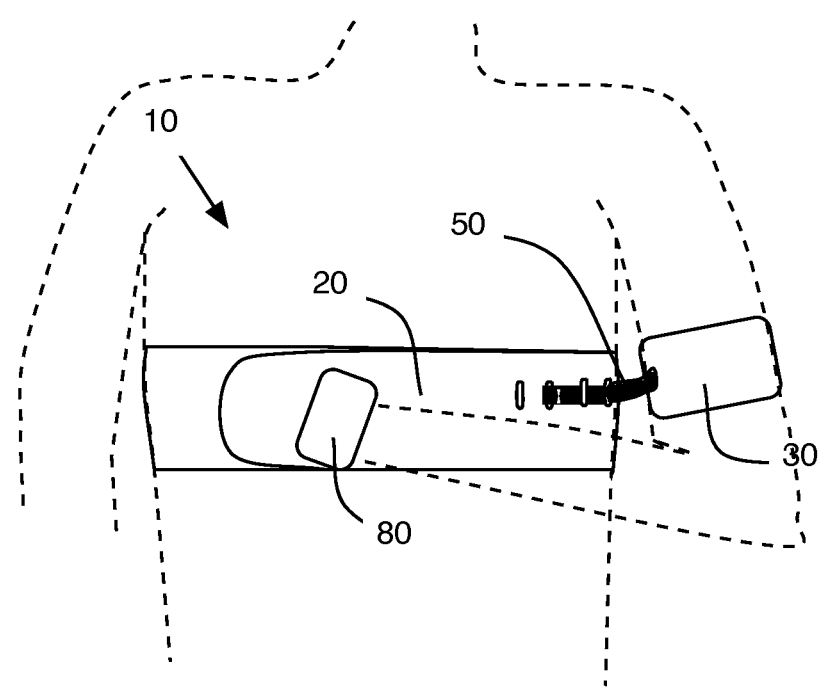
FIG. 1 is a front view in situ of a first preferred embodiment according to the present invention.

FIG. 1 illustrates one preferred embodiment of the present invention 10 as would be worn, typically by a post-operative patient in the first 12 to 72 hours recovering from a pacemaker implant when most lead dislodgements occur. This time period is particular crucial to recovery. The present invention recognizes that some movement of the patient's arm (can be either arm but usually left) is desired, but the movement should be significantly restricted to about 0-degrees (arm extending downward generally parallel to the long axis of the body) to about 45 degrees rotation in the coronal plane wherein 90-degrees would be parallel to the axial plane. Similarly, movement of the arm is restricted to about a total of 45-degrees in the Sagittal plane. Accordingly, the present invention restricts the movement of the patient's arm within this zone by means of a chest band 20 encircling the chest and or abdomen and back of the patient and a cuff 30 adapted to loosely encircle the upper arm of the patient. The cuff 30 and chest band 20 connect by means of an adjuster strap 50, which fixably couples to the cuff and releasably couples to the chest band 20 by means of a (see, e.g. FIG. 2) hoop 28 through which a free end of the strap 50 extends and attaches to a hook-and-loop fastener material 26 on the chest band 20. In an alternative embodiment the free end folds back on itself and tucks into a provided pocket.

The present invention 10 includes a torso support band 20, generally a rectilinear swatch of cloth having two, opposing free ends. The band adapts to arrange circumferencially about the chest or upper torso of a human patient. To accommodate varying sized patients, the torso support band, or chest band 20, is of sufficient length to allow the two opposed ends to overfold. One well-suited material for the torso support band includes the material available under the trade name Veltex (a black colored material has a model number 503, but other colors would work equally well and may be preferred for other applications or for the tastes of the patient) available from Velcro USA Inc. of Manchester N.H. This type of fabric is also known as display fabric or tempo-loop fabric. This fabric releasably engages the hook-side of common hook-and-loop fasteners (such as Velcro brand fastener). To prevent the edge of the fabric from fraying, stitching or applying a fabric binding along the edge or other common techniques well-understood in the fabric and apparel industries may be incorporated in the chest band or other fabric components including the arm cuff 30 and wrist cuff 80. A preferred embodiment alternatively uses a tri-laminate material consisting of a distal layer of a loop material or fabric well-suited to selectively couple to a hook material, an inner layer of foam for structure and padding, and a proximal layer of a lycra-like or spandex-like material to stabilize and bind to the foam layer, and all of these layers are laminated together as would be well-understood in the art. The tri-laminate material includes a binding material mechanically fastened (sewn) to the edges of the band and cuffs.

This wrist cuff adjusts for overall diameter using a hook and loop fastener closure system, similar to the means discussed for the arm cuff and chest band. This adjustment enables the wrist cuff to be sized for different sized wrists, and to be adjusted for comfort (looser) or for security (tighter), and preferably is fit rather snuggly. The wrist cuff may optionally include a second adjuster strap (not shown in the drawings), which is similar to arm band adjuster strap. One end of this second adjuster strap fixabley couples to the wrist cuff 80, while the second end includes a hook fastener to selectively couple to the chest band.

Figure 2:
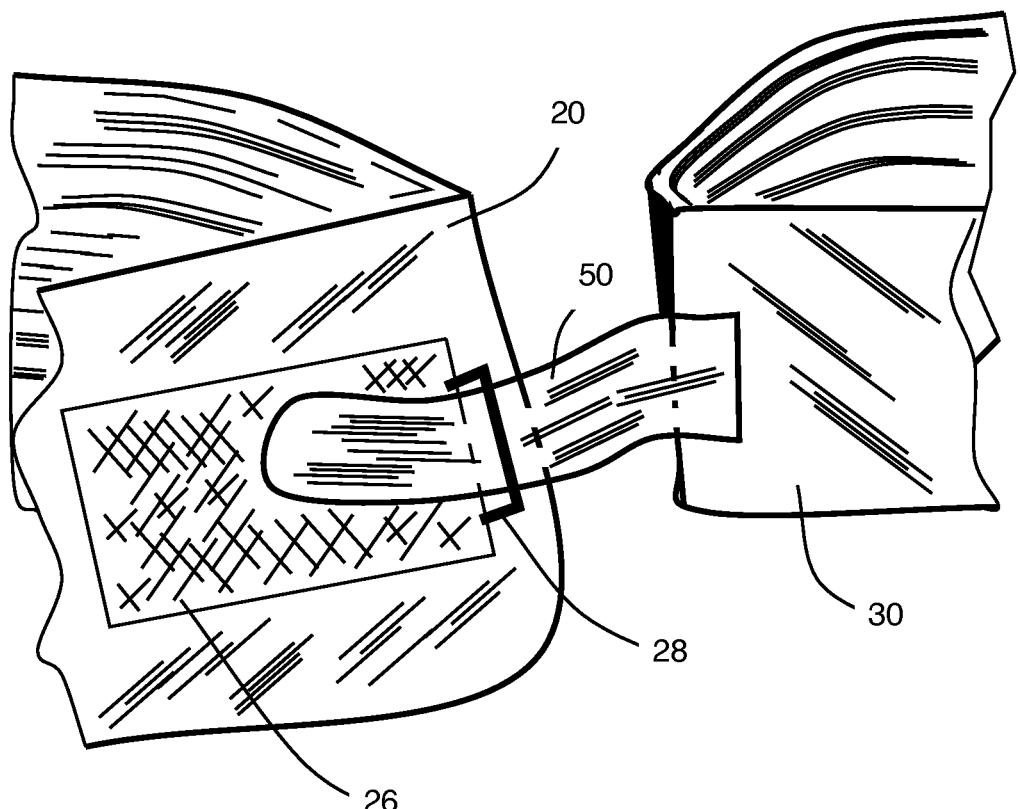
FIG. 2 is a partial front view detailing certain components of the embodiment of FIG. 1.

FIG. 2 details a portion of the front of the post-operative pectoral pocket immobilization device 10 of the present invention. Specifically, FIGS. 2 and 5 highlight the adjuster strap 50 which is nylon having a hook fastener attached. It may be doubled sided comprising a double sided hook and loop fastener material. In one preferred embodiment, the adjuster strap 50 comprises a first end 51 including a hook side of a hook-and-loop fastener system (the hook side releasably engages the chest band) and a second end 55 having a smooth nylon webbing. The strap is ideally 1¾-inches wide and about 4-8 inches long. Intermediate to the two ends, a stop feature 53 to prevent the smooth end from passing through a feature on the chest band.

One end of the strap 50 (a non-resilient strap member) is fixable coupled to the arm cuff 50 by known fastening means such as sewn to the fabric cuff. This arm cuff can be made from the same Veltex or tri-laminate material as the chest band. Other means of fixably fastening would also work, such as riveting, or gluing. Alternatively, the strap can be removably coupled to the cuff by many known means including a hook and loop fastener, button, snap, zipper and the like. The opposite end, or free end of the strap, adapts to connect through a hoop 28 on the chest band 20. The hoop is ideally plastic or metal, however other materials would work equally well.

In alternative embodiments a plurality of hoops or buttonholes can be affixed or cut or sewn to the chest band to allow greater adjustability. Further, an option patch of hook and loop like material 26 arranges on the chest band adjacent to the hoop 28 to prevent the loose end from dangling and more importantly to releasably secure the strap to maintain the arm cuff in a selected position relative to the chest band.

Figure 3:
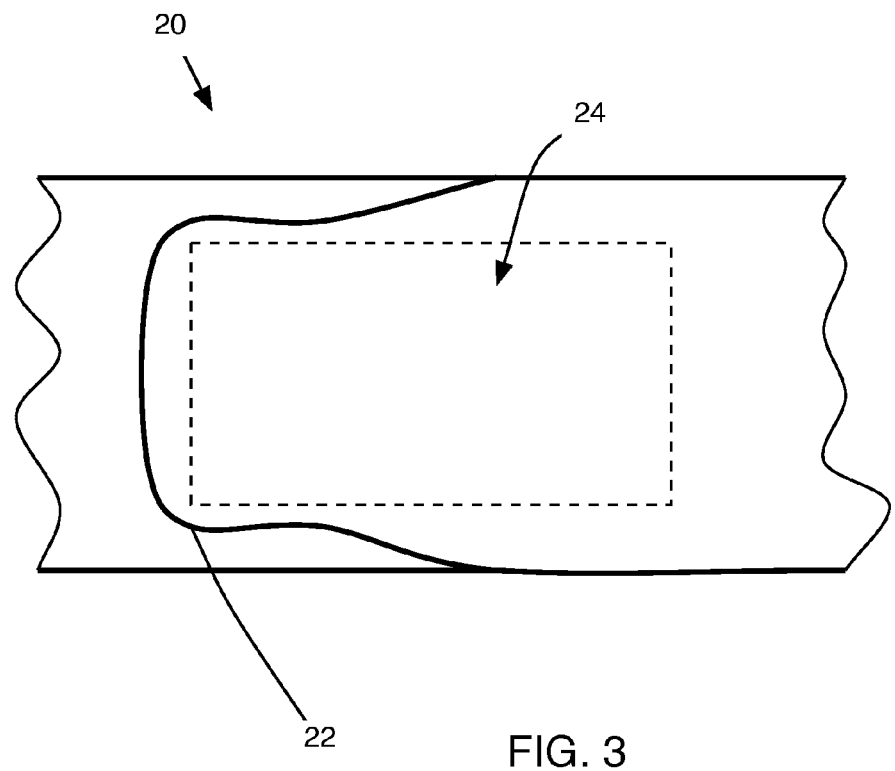
FIG. 3 is a partial front view detailing certain other components of the embodiment of FIG. 1.

FIG. 3 details the overlapping ends of the chest band 20. The inside or proximal surface of one end of the chest band includes a hook and loop fastener material 24 that is adapted to engage the fabric of the exterior face (distal side) of the opposite end of the chest band. In this embodiment, the patch of Hook and loop 24 selectively engages the material directly, allowing for a wide range of adjustability and does not require a mating piece of hook and loop material. Obviously, in alternative embodiments the hook and loop material can mate to an associated patch of mating hook and loop, or the location of the pieces could be interchanged. As illustrated in FIG. 3, the first overlapping end includes a slight taper. This taper prevents the hook and loop patch 24 from catching on clothing worn by the patient and provides a tab at the end for patient/user to grab for easy removal of the device.

Figure 4:
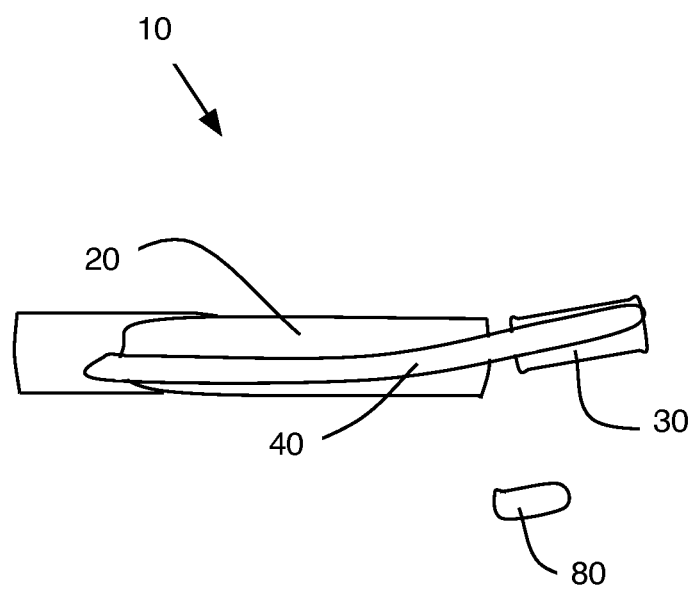
FIG. 4 is a front view of the first preferred embodiment and includes an immobilizer band.

FIG. 4 shows an optional immobilizer band 40. This band wraps around a portion of the torso including the chest and the back, or totally circles the upper torso, and arm cuff of the patient to hold fast the arm in a downward position and is ideally suited for use when the patient is asleep and no movement of the arm is desired or in other circumstances where restricted movement is required.

Figure 5:
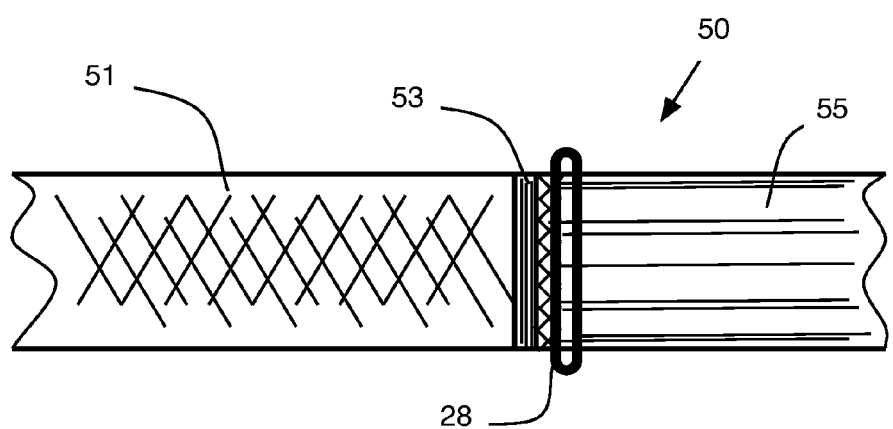
FIG. 5 is a partial front view detailing the adjuster strap of the embodiment of FIG. 1.

FIG. 5 details one preferred adjuster strap 50. This strap includes a first end sewn or otherwise fixably coupled to the armband 30. This first end includes a smooth nylon webbing 55 to better allow the strap to slideably insert on a feature on the chest band 28 (the chest band is not shown in FIG. 5, but is understood to be attached to the strap 50 at hoop 28), such as a hoop, button-hole, or other fastener (buckle, clip, etc.). A second end includes a single-sided hook-type material 51. The hook side of this second end engages the chest band 20 to enable selective coupling of the second end. A ridge 53 intermediate to the two ends of the strap prevents over-travel of the strap through the hoop 28.

Figure 6:
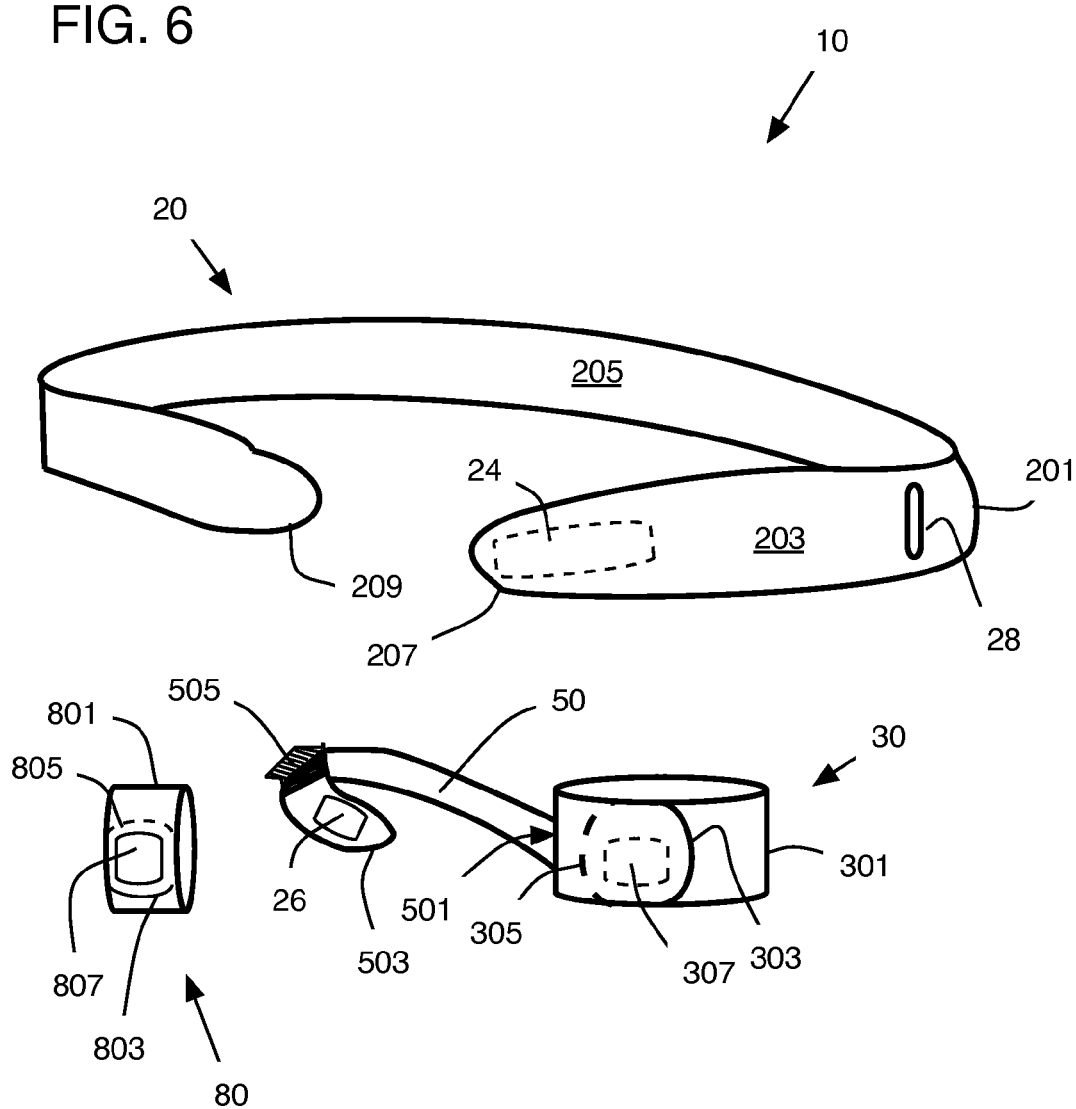
FIG. 6 is an exploded view of components of another embodiment of the present invention.

A contemplated preferred embodiment of the present invention includes a system 10 for restricting movement of an arm, wrist, and shoulder, as FIG. 6 illustrates, for example. The system comprises a chest band 20 comprising a strap body 201 having a distal surface 203 and a proximal surface 205 and a short end 207 (closest to the arm cuff and includes the hook and loop fastener for the adjuster strap) oppositely disposed from a long end 209, and the proximal surface of the short end having a means 24 for selectively coupling to the long end, and an adjuster element 28 disposed on the distal surface of the strap body adjacent to the short end. The system further includes an arm cuff 30 comprising a cuff body 301 having oppositely disposed arm-cuff ends (303 305) adapted to overlap, wherein the overlap further includes means 307 for selectively coupling the arm-cuff-ends together. The system also includes a non-resilient strap member 50 coupled to the arm cuff 30 at a first end 501, the strap further having a second free 503 end including a fastening means 26, the strap second free end extending through the adjuster element provided by the upper chest band, the strap second end adapted to selectively couple to the distal surface of the chest band. Adjacent to the free-end 503 of the strap, a retention feature 505 is included to prevent the strap free-end from being pulled back-through the adjuster element 28.

The system 10 also includes a wrist cuff 80 comprising a rectilinear wrist-body 801 having a first wrist-cuff-end 803, an opposite second wrist-cuff-end 805, and means for selectively coupling the first wrist-cuff-end to the second wrist-cuff-end (not shown in FIG. 6, but similar in construction and operation as the arm cuff means 307, as would be understood in the art), the wrist cuff further comprising fastening means 807 for selectively coupling the wrist cuff to the chest band.

One particular advantage of the present invention over the known art is that a patient can one-handedly put the device 10 on and self-adjust it.

The arm cuff 30 couples to the chest band 20 by means of the adjuster strap 50 and they cannot be separated, preventing confusion with elderly patients later. The device will initially be put on by hospital staff with instructions for usage. The arm cuff can be fitted and trimmed (one size fits all) if necessary. The arm cuff will then be fitted and not changed unless patient wants to put over thick clothing, such as a coat, later. When patients are alone later and want to put device back on, they simply put their arm thru the arm cuff and pull it up above the elbow. They will then place ends of chest band 20 around torso and connect in front. They, optionally may put their wrist in the wrist cuff 80 and secure. To remove, they will unwrap wrist cuff 80 if worn, then they will unhook the chest band 20 and slide arm cuff 50 down and off the arm.

Accordingly, the patient would first slip on the loose fitting arm cuff over the arm and place it on the upper arm using the right hand. The material of the arm cuff provides sufficient frictional contact between the arm cuff and the wearer's arm or clothing to locate it without much effort in holding it in place. Then, the patient places the second (short) end of the chest band 20 under the left armpit applying pressure to hold the arm cuff in position. This captures both the short end of the chest band and the arm cuff. The short end would be placed so that the terminus was about centered on the midline of the chest. Then, the first (long) end of the chest band is drawn across the short end and the hook and loop patch 24 engages the short end. Next, the patient grabs the free end of the adjuster strap 50, which is pre-threaded through the hoop 28 and folds it over itself or attaches it to the hook and loop strip 26 or directly to the distal side of the chest band so that the arm cuff is positioned relative to the chest band.

One contemplated method of using the various preferred embodiments includes placing the device 10 on a patient post-operatively to immobilize or restrict movement of the arm and shoulder after a pacemaker or ICD implant surgery.

A preferred embodiment according to the present invention contemplates a system (see, for example, FIG. 6) and method for preventing cardiac device leads from dislodging post operatively. This comprises wearing a post-operative pectoral-pocket immobilization device 10. This device comprises a chest band 20 adapted to be fit externally around the chest just below the rib cage of the upper torso of a patient, the chest band comprising a strap body 201 having a distal surface 203 and a proximal surface 205 and a short end 207 oppositely disposed from a long end 209, and the proximal surface of the short end having a means 24 for selectively coupling to the long end. The device further includes an arm cuff 30 adapted to be fit around the upper arm of the patient, the arm cuff comprising a cuff body having oppositely disposed arm-cuff ends adapted to overlap, wherein the overlap further includes means for selectively coupling the arm-cuff-ends together; a non-resilient adjuster-strap member coupled to the arm cuff at a first strap-end, the strap further having a second strap-end including a strap-fastening means, the second strap-end extending through an adjuster element provided by the upper chest band, the second strap-end adapted to selectively couple to the chest band whereby lateral movement of the arm cuff is restricted based on the amount of strap extending between the arm cuff and the adjuster element, the strap member adapted to restrict movement of the upper arm relative to the upper torso; and a wrist cuff adapted to selectively secure to a wrist of the upper arm having the arm cuff, the wrist cuff including a rectilinear wrist-body having a first wrist-cuff-end, an opposite second wrist-cuff-end, and means for selectively coupling the first wrist-cuff-end to the second wrist-cuff-end, the wrist cuff further comprising fastening means for selectively coupling the wrist cuff to the chest band. Additionally, the wrist cuff may be further secured to the chest band with a second adjustable strap.

Each major component, the chest band, the wrist cuff and the arm cuff, is preferably a tri-laminate material comprising a distal layer consisting of a loop material, an inner foam layer for structure and padding, and a proximal layer consisting of a spandex-like or lycra-like material for binding to and stabilizing the foam layer. The distal layer being a loop type material is well suited for a hook type fastener (such as Velcro-brand or other generally known hook and loop fastener) to selectively couple to the distal layer. Thus, a hook portion of the hook and loop fastener can be coupled to the proximal layer so that overlapping ends of the chest band, wrist cuff, or arm cuff can adjustably couple to the proximal layer without requiring a secondary material. Of course, this could be reversed and the hook material could be placed on the distal layer and the hoop portion on the proximal layer.

The method further contemplates that the fastening means for selectively coupling the wrist cuff to the chest band comprises a hook-and-loop fastener surface exposed on an exterior portion of the wrist-body so to selectively couple to the distal surface of the chest band; overlapping and selectively coupling the arm-cuff-ends together to form a tubular member with an open center portion defined by at least one sidewall formed by the overlapped arm cuff body and the tubular member adapted to slide over the lower arm and elbow of the patient wherein the means for selectively coupling the arm-cuff-ends together includes a hook-and-loop fastener; and allowing the arm cuff to slide freely up and down the upper arm above the elbow and below the shoulder.

The method further includes that the adjustable strap having a free end extending from the arm cuff is coupled to the chest band by inserting the free end through the chest-band adjuster element (hoop 28) pulling the free end away from the chest band until the arm cuff is directly adjacent to the chest band, then the strap free end is secured to the chest band by the Hook and loop-type fastener element on the strap free and couples to the chest band.

The method also contemplates that the wrist cuff is selectively coupled to the chest band. And, the method includes that the means for selectively coupling the first wrist-cuff-end to the second wrist-cuff-end further includes shaping the wrist cuff body into a loop and sliding the loop over the wrist of the patient.

Although the invention has been particularly shown and described with reference to certain embodiments, it will be understood by those skilled in the art that various changes in form and detail may be made without departing from the spirit and scope of the invention. And, although claims are not required, I claim at least:

I claim:

1. A pectoral-pocket immobilization device system for a cardiac device implant surgery patient, the cardiac device having leads, the system comprising:
   a chest band configured to be fit externally around of the upper torso of a patient, the chest band comprising a strap body having a distal surface and a proximal surface and a short end oppositely disposed from a long end, and the proximal surface of the short end having a means for selectively coupling to the long end;
   an arm cuff configured to be fit around the upper arm of the patient, the arm cuff comprising a cuff body having oppositely disposed arm-cuff ends configured to overlap, wherein the overlap further includes means for selectively coupling the arm-cuff-ends together;
   a non-resilient adjuster-strap member coupled to the arm cuff at a first strap-end, the strap further having a second strap-end including a strap-fastening means, the second strap-end extending through an adjuster element provided by the upper chest band, the second strap-end configured to selectively couple to the chest band whereby lateral movement of the arm cuff is restricted based on the amount of strap extending between the arm cuff and the adjuster element, the strap member configured to restrict movement of the upper arm relative to the upper torso by means of the arm cuff wherein the adjuster-strap member selectively couples to the chest band from a first operable position representing about 0-degrees (arm extending downward generally parallel to the long axis of the body) to a second operable position representing about 45-degrees rotation in the coronal plane and wherein the arm can be selectively engaged to the chest band by means of the adjuster-strap member at any position between the first and second operable positions; and
   a wrist cuff configured to selectively secure to a wrist of the upper arm having the arm cuff, the wrist cuff including a rectilinear wrist-body having a first wrist-cuff-end, an opposite second wrist-cuff-end, and means configured to selectively couple the first wrist-cuff-end to the second wrist-cuff-end, the wrist cuff further comprising a fastening means for selectively coupling the wrist cuff to the chest band;
   wherein the pectoral immobilization device system is configured to be worn post-operatively by the patient 12 to 72 hours after the cardiac device implant surgery and is configured to prevent the cardiac device leads from dislodging post-operatively.

2. The system of claim 1 further comprising:
   the fastening means for selectively coupling the wrist cuff to the chest band comprises a hook-and-loop fastener surface exposed on an exterior portion of the wrist-body so to selectively couple to the distal surface of the chest band;
   whereby the system is configured to enable the arm-cuff-ends to overlap and selectively couple together to form a tubular member with an open center portion defined by at least one sidewall formed by the overlapped arm cuff body and the tubular member adapted to slide over the lower arm and elbow of the patient wherein the means for selectively coupling the arm-cuff-ends together includes a hook-and-loop fastener; and
   whereby the system is configured to allow the arm cuff to slide freely up and down the upper arm above the elbow and below the patient's shoulder.

3. The system of claim 2 wherein:
   the adjustable strap is configured to selectively position the arm cuff relative to the chest band whereby the adjustable strap has a free end extending from the arm cuff, the strap free end is selectively positioned and secured to the chest band by the hook and loop-type fastener element on the strap free and couples to the chest band.

4. The system of claim 2 wherein:
   the wrist cuff is configured to selectively couple to the chest band.

5. The system of claim 2 wherein:
   the means configured to selectively coupling the first wrist-cuff-end to the second wrist-cuff-end further includes shaping the wrist cuff body into a loop around the wrist.

6. A pectoral-pocket immobilization device system for a cardiac device having leads, the cardiac device being implanted in a patient, the system comprising:
   a chest band configured to be fit externally around of the upper torso of a patient, the chest band comprising a strap body having a distal surface and a proximal surface and a short end oppositely disposed from a long end, and the proximal surface of the short end having a means for selectively coupling to the long end;
   an arm cuff configured to be fit around the upper arm of the patient, the arm cuff comprising a cuff body having oppositely disposed arm-cuff ends configured to overlap, wherein the overlap further includes means for selectively coupling the arm-cuff-ends together;
   a non-resilient adjuster-strap member coupled to the arm cuff at a first strap-end, the strap further having a second strap-end including a strap-fastening means, the second strap-end extending through an adjuster element provided by the upper chest band, the second strap-end configured to selectively couple to the chest band whereby lateral movement of the arm cuff is restricted based on the amount of strap extending between the arm cuff and the adjuster element, the strap member configured to restrict movement of the upper arm relative to the upper torso by means of the arm cuff wherein the adjuster-strap member selectively couples to the chest band from a first operable position representing about 0-degrees (arm extending downward generally parallel to the long axis of the body) to a second operable position representing about 45-degrees rotation in the coronal plane and wherein the arm can be selectively engaged to the chest band by means of the adjuster-strap member at any position between the first and second operable positions; and a wrist cuff configured to selectively secure to a wrist of the upper arm having the arm cuff, the wrist cuff including a rectilinear wrist-body having a first wrist-cuff-end, an opposite second wrist-cuff-end, and means configured to selectively couple the first wrist-cuff-end to the second wrist-cuff-end, the wrist cuff further comprising a fastening means for selectively coupling the wrist cuff to the chest band;

wherein the system is configured to be worn post-operatively by the patient and is configured to enable the patient's arm and shoulder to have range of motion without the leads from a cardiac device being dislodged post-operatively.

7. The system of claim 6 wherein:

the fastening means for selectively coupling the wrist cuff to the chest band comprises a hook-and-loop fastener surface exposed on an exterior portion of the wrist-body so to selectively couple to the distal surface of the chest band;

whereby the system is configured to enable the arm-cuff-ends to overlap and selectively couple together to form a tubular member with an open center portion defined by at least one sidewall formed by the overlapped arm cuff body and the tubular member adapted to slide over the lower arm and elbow of the patient wherein the means for selectively coupling the arm-cuff-ends together includes a hook-and-loop fastener; and whereby the system is configured to allow the arm cuff to slide freely up and down the upper arm above the elbow and below the patient's shoulder.

8. The system of claim 6 wherein:

the adjustable strap is configured to selectively position the arm cuff relative to the chest band whereby the adjustable strap has a free end extending from the arm cuff, the strap free end is selectively positioned and secured to the chest band by the hook and loop-type fastener element on the strap free and couples to the chest band.

9. The system of claim 7 wherein:

the wrist cuff is configured to selectively couple directly to the chest band.

* * * * *